United States Patent [19]

Krementsov

[11] Patent Number: 5,747,688

[45] Date of Patent: May 5, 1998

[54] DYNAMOMETER FOR DETERMINING HUMAN FORCE

[76] Inventor: Yuriy Krementsov, 110-11 Queens Blvd., Forrest Hills, N.Y. 11375

[21] Appl. No.: 730,034

[22] Filed: Oct. 15, 1996

[51] Int. Cl.[6] ................................................. G01L 3/24
[52] U.S. Cl. ................................................. 73/379.01
[58] Field of Search .................... 73/379.01, 862.541, 73/862.625, 862.56, 379.09; 128/774; 482/92–95, 121–123, 125–127, 133

[56] References Cited

U.S. PATENT DOCUMENTS

| | | | |
|---|---|---|---|
| 712,072 | 10/1902 | Jordan | 73/379.01 |
| 954,790 | 4/1910 | Ertl | 73/379.01 |
| 3,364,747 | 1/1968 | Ebstein | 73/379.01 |
| 3,640,530 | 2/1972 | Henson et al. | 73/379.01 |
| 3,929,331 | 12/1975 | Beeding | 73/862.08 X |
| 4,667,513 | 5/1987 | Konno | 73/379.01 |
| 4,912,638 | 3/1990 | Pratt, Jr. | 482/92 X |
| 5,275,045 | 1/1994 | Johnston et al. | 73/379.01 |

*Primary Examiner*—Elizabeth L. Dougherty
*Attorney, Agent, or Firm*—Ilya Zborovsky

[57] ABSTRACT

A dynamometer for determining a force applied by a human has a pulling element adapted to be pulled by a user, an indicating device indicating a force applied by a user to the pulling element, a transmission element for connecting the pulling element with the indicating means so that the indicating device indicate the force in response to the application of force by a user to the pulling element, and a recorder for recording a course of changes of the force over time and connected with the transmission element.

4 Claims, 2 Drawing Sheets

PRIOR ART

DYNAMOMETER FOR DETERMINING HUMAN FORCE

BACKGROUND OF THE INVENTION

The present invention generally relates to dynamometers for use by individuals.

Dynamometers of the above mentioned general type are known in the art. The dynamometer has an element which is held by a user and pulled by him, and an indicating device which indicates a force applied by the user during pulling. One of such dynamometers which is identified as a back-leg-chest dynamometer PCT5039B is disclosed for example in the catalog of Preston, 1993–1994, P.O. Box 89, Department 1337, Jackson, Mich. 49204. The dynamometer provides adequate indication of the force applied by the user. However, the values of the force applied by the user are instantaneous values. The dynamometer of the above mentioned type does not provide the information about a course of a force application over time and therefore information about the essential characteristics of the user's strength, health condition, and state.

SUMMARY OF THE INVENTION

Accordingly, it is an object of present invention to provide a dynamometer of the above mentioned general type, which is a further improvement and provides a more detailed information about the user's strength, health condition, and state.

In keeping with these objects and with others which will become apparent hereinafter, one feature of present invention resides, briefly stated in a dynamometer which has an element to be pulled by a user; and indicating device which indicates a force applied by the user during pulling of the pulling element and operative through a transmission element between the pulling element and the indicating device, and means connected with said transmission element and operative by said transmission element continuously for showing a force applied by the user to said pulling element over a period of time.

When the dynamometer is designed in accordance with the present invention, it shows a course of the force application, for example changes of force in time, a speed of force application, an amplitude of force, a time of force application, etc. Therefore, the dynamometer shows better the nature of the force application, the health conditions, the strength, and other important characteristics of the user.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
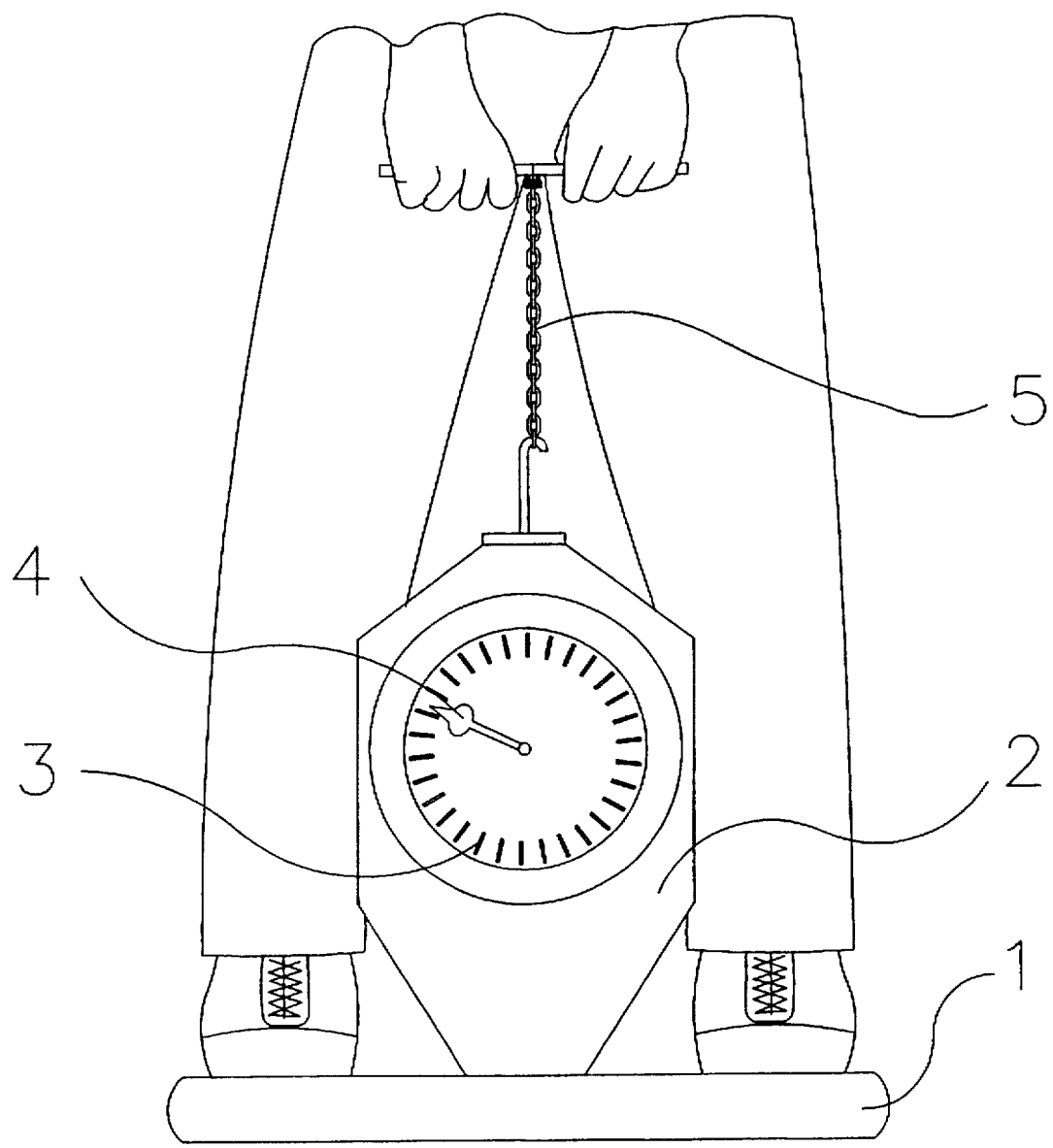
FIG. 1 is a view from outside of a dynamometer in accordance with the present invention.
Figure 2:
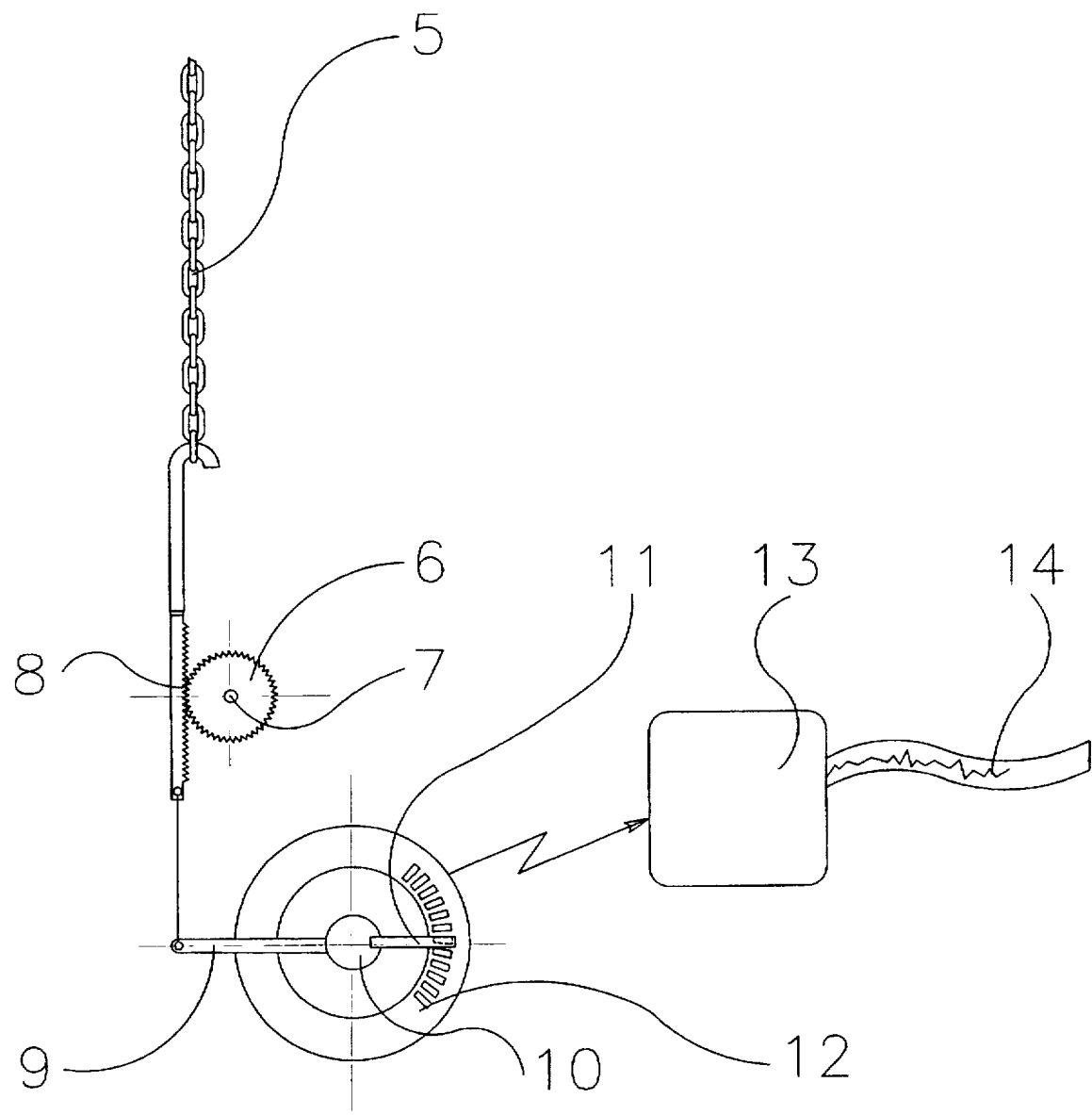
FIG. 2 is a view showing a part of the dynamometer which provides a continuous indication of a force over time.

A dynamometer in accordance with present invention has a substantially horizontal support to be placed on a floor or the like, and a housing arranged on the support and identified with the reference numeral 2. A housing accommodates several components of the dynamometer. The dynamometer further has an indicating device which is formed as a scale 3 provided with a pointer 4. A pulling element 5 is connected through a transmission element with the axle of the pointer 4, so that when the user pulls the pulling element 5, the pointer 4 turns relative to the scale and its free end points to a corresponding graduation mark and a number near the weak to identify the force applied by the user.

The transmission element can be formed as a toothed gear 6 which carries the axle 7 of the pointer and is engaged with the toothed rack 8 connected with the pulling element 5. The other end of the toothed rack 5 is connected with a handle 9 of a rheostat which has a central core 10 provided with a sliding contact 11, and an outer ring 12 having a cross-section with a changing radial dimension over the circumference of the ring. When the toothed rack 8 is pulled through the pulling element by the user, it displaces the handle 9 and therefore the core 10 connected with the handle, together with the contact 11, the contact 11 is displaced relative to the ring 12 so as to provide an electrical contact in different thickness areas of the ring 12 and therefore to produce different electrical signals depending on the position of the contact 11, which depends on the position of the toothed rack 8 and therefore on the force applied by the user to the pulling element 5. Therefore, depending on the applied force, the rheostat produces different electrical signals.

A known strip-chart recorder 13 is connected with the rheostat and receives electrical signals from it. The strip-chart recorder has a known pen which cooperates with a paper band 14 dischargeable from the recorder. Under the action of the electrical signals supplied from the rheostat, the pen of the strip-chart recorder produces a chart on the paper band 14, which shows changes of a force applied by the user over time. These changes show a magnitude of force applied over time, its amplitude, the speed of force application, the time of force application, etc. Therefore a very detailed information is provided in the inventive dynamometer which was not provided before.

It will be understood that each of the elements described above, or two or more together, may also find a useful application in other types of constructions differing from the types described above.

While the invention has been illustrated and described as embodied in dynamometer for determining humans force, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

What is claimed is:

1. A dynamometer for determining a force applied by a human, comprising a pulling element adapted to be pulled by a user; indicating means indicating a force applied by a user to said pulling element; transmission means for connecting said pulling element with said indicating means so that said indicating means indicate the force in response to the application of force by a user to said pulling element; and means for recording a course of changes of the force over time and connected with said transmission means, said signal producing means being formed as a rheostat having a handle connected with said first transmission element; a central core provided with an electrical contact and turnable by said handle, and an outer ring having a changing radial cross-section and contactable by said contact upon the displacement of said first transmission element, so that when said electrical contract is turned and provides a contact between said core and different portions of said ring having a different thicknesses said signal producing means produce different electrical signals and supply them to said strip-chart recorder.

2. A dynamometer as defined in claim 1, wherein said recording means include a strip-chart recorder connected with said transmission means.

3. A dynamometer as defined in claim 2, wherein said indicating means includes a scale and a pointer turnable relative to said scale, said transmission means including a first transmission element which is rectilinearly displaceable by said pulling element, and a second transmission element which is turnable by said first transmission element and connected with said pointer for turning said pointer; and further comprising electrical signal producing means connected with said first transmission element so that upon a displacement of said first transmission element said signal producing means produce electrical signals, said signal producing means being connected with said strip chart recorder so as to send said electrical signals to said strip chart recorder.

4. A dynamometer as defined in claim 1, wherein said strip-chart recorder has a movable record carrier, so that in response to said electrical signals, a chart is produced on said movable record carrier in correspondence with changes in a force applied by the user over time.

* * * * *